US012611411B2

(12) United States Patent
Weisenthal et al.

(10) Patent No.: US 12,611,411 B2
(45) Date of Patent: Apr. 28, 2026

(54) TRIPLE-AGENT THERAPY FOR CANCER TREATMENT

(71) Applicant: CYTOMETRIC THERAPEUTICS, INC., Dover, DE (US)

(72) Inventors: Larry Weisenthal, Huntington Beach, CA (US); William Grace, Plandome, NY (US)

(73) Assignee: CYTOMETRIC THERAPEUTICS, INC., Dover, DE (US)

( * ) Notice: Subject to any disclaimer, the term of this patent is extended or adjusted under 35 U.S.C. 154(b) by 0 days.

(21) Appl. No.: 18/689,980

(22) PCT Filed: Sep. 15, 2022

(86) PCT No.: PCT/US2022/043601
§ 371 (c)(1),
(2) Date: Mar. 7, 2024

(87) PCT Pub. No.: WO2023/043883
PCT Pub. Date: Mar. 23, 2023

(65) Prior Publication Data
US 2025/0127791 A1 Apr. 24, 2025

Related U.S. Application Data

(60) Provisional application No. 63/244,412, filed on Sep. 15, 2021.

(51) Int. Cl.
| | |
|---|---|
| *A61K 31/5377* | (2006.01) |
| *A61K 31/00* | (2006.01) |
| *A61K 31/138* | (2006.01) |
| *A61K 31/4745* | (2006.01) |
| *A61K 31/475* | (2006.01) |
| *A61P 35/00* | (2006.01) |

(52) U.S. Cl.
CPC ........ *A61K 31/5377* (2013.01); *A61K 31/138* (2013.01); *A61K 31/4745* (2013.01); *A61P 35/00* (2018.01)

(58) Field of Classification Search
CPC .............. A61K 31/5377; A61K 31/138; A61K 31/4745; A61K 2300/00; A61P 35/00
See application file for complete search history.

(56) References Cited

U.S. PATENT DOCUMENTS

| | | | |
|---|---|---|---|
| 8,663,643 B2 | 3/2014 | Berry et al. | |
| 2010/0189683 A1 | 7/2010 | Holmlund et al. | |
| 2015/0088432 A1* | 3/2015 | Sanborn ................. | G16B 30/10 702/20 |

FOREIGN PATENT DOCUMENTS

WO 2015048546 A1 4/2015

OTHER PUBLICATIONS

Mimeault et al., "Recent Advances on the Molecular Mechanisms Involved in the Drug Resistance of Cancer Cells and Novel Targeting Therapies", Clinical Pharmacology & Therapeutics (2008); 83, 5, 673-691 (Year: 2008).*
Godoy et al., "AUA 2019: Phase II Trial of Estrogen Receptor Targeted Treatment of Non-Muscle Invasive Bladder Cancer with Tamoxifen", AUA 2019, May 3-6, 2019 (Year: 2019).*
Dominguez-Escrig et al., "Evaluation of the Therapeutic Potential of the Epidermal Growth Factor Receptor Tyrosine Kinase Inhibitor Gefitinib in Preclinical Models of Bladder Cancer", Clinical Cancer Research, vol. 10, 4874-4884, Jul. 15, 2004 (Year: 2004).*
Arnold et al., "Vinorelbine in bladder-preserving multimodality treatment for muscle-invasive bladder cancer-a valid option for cisplatin-unfit patients?", Strahlenther Onkol 198, 25-32 (2022). Published Aug. 19, 2021 (Year: 2021).*
Nair et al., "A simple practice guide for dose conversion between animals and human", J Basic Clin Pharm. Mar. 2016;7(2):27-31 (Year: 2016).*
"Definition of Body surface area", https://www.rxlist.com/body_surface_area/definition.htm (Year: 2021).*
National Cancer Institute dictionary, https://www.cancer.gov/publications/dictionaries/cancer-terms/def/regimen (Year: 2018).*
Bartsch, Oral vinorelbine: pharmacology and treatment outcome in nonsmall cell bronchial carcinoma and breast carcinoma, Onkolgie, Suppl 1:1-28, 2006. doi: 10.1159/000091889. (English Abstract Submitted).
Kaklamani et al., New Targeted Therapies in Breast Cancer, Seminars in Oncology, 31(2) Suppl 4: 20-25, 2004.
Wong, Emerging treatment combinations: Integrating therapy into clinical practice, Am J Health-Syst Pharm, 66, Suppl 6:S9-S14, 2009. DOI 10.2146/ajhp090439.
Weisenthal, "Differential Staining Cytotoxicity Assay: A Review, Cancer Cell Culture: Methods and Protocols", Second Edition, Methods in Molecular Biology (Chapter 22), Cree (Ed.), 2011.
Wagner, et al., Gefitinib in combination with tamoxifen in patients with ovarian cancer refractory or resistant to platinum-taxane based therapy—A phase II trial of the AGO Ovarian Cancer Study Group (AGO-OVAR 2.6) Gynecologic Oncology, Dec. 11, 2006, vol. 105, pp. 132-137.
Miller, et al., "Understanding the mechanisms of aromatase inhibitor resistance", Breast Cancer Research, Jan. 19, 2012, vol. 14:201, pp. 1-14.

(Continued)

*Primary Examiner* — Renee Claytor
*Assistant Examiner* — Elena V Vishnyakova
(74) *Attorney, Agent, or Firm* — BakerHostetler

(57) ABSTRACT

Disclosed are methods of treating cancer with a tri-agent therapy. The methods include a cancer treatment regimen with two or three different antineoplastic medications, including tamoxifen, gefitinib, and vinorelbine (TGV). The cancer treatment regimen can include sequential and/or concurrent administration of tamoxifen, gefitinib, and vinorelbine. The cancer treatment regimen can include sequential and/or concurrent administration of tamoxifen and gefitinib as adjuvants to a prescribed treatment. The cancer treatment regimen can be cyclical or can be a continuous metronomic treatment with metronomic dosing. The cancer treatment regimen can be cyclical and then can be followed by a continuous metronomic treatment with metronomic dosing.

21 Claims, No Drawings

(56) References Cited

OTHER PUBLICATIONS

Tormey, et al., "Evaluation of Tamoxifen Doses with and without Fluoxymesterone in Advanced Breast Cancer", Annals of Internal Medicine, 1983, vol. 98, No. 2, pp. 139-144.

Daw, et al., "Phase I and Pharmacokinetic Study of Gefitinib in Children with Refractory Solid Tumors: A Children's Oncology Group Study", Journal of Clinical Oncology, Sep. 1, 2005, vol. 23, Iss. 25, pp. 6172-6180.

International Search Report and Written Opinion issued in International Patent Application No. PCT/US2022/043601, mailed Jan. 5, 2023.

International Patent Application No. PCT/US2022/043601; Int'l Preliminary Report on Patentability; dated Mar. 28, 2024; 11 pages.

Gioulbasanis et al.; "Gefitinib in Combination with Gemcitabine and Vinorelbine in Patients with Metastatic Breast Cancer Pretreated in Taxane and Anthracycline Chemotherapy: A Phase I/II Trial"; Anticancer Research; vol. 28; 2008; p. 3019-3025.

* cited by examiner

TRIPLE-AGENT THERAPY FOR CANCER TREATMENT

CROSS-REFERENCE TO RELATED APPLICATIONS

The present application is the National Stage Application of International Patent Application No. PCT/US2022/043601, filed Sep. 15, 2022, which claims priority to and the benefit of U.S. Provisional Patent Application No. 63/244,412 filed on Sep. 15, 2021, the entirety of each of which is incorporated herein by reference.

TECHNICAL FIELD

The disclosure relates to a triple-agent therapy for systemic treatment of cancer, particularly to the combination of tamoxifen, gefitinib, and vinorelbine ("TGV") in the treatment of a broad range of cancers.

BACKGROUND

Many types of cancer treatments have been developed to combat cancer. The treatments may vary from patient to patient and may include a biomarker test to establish which cancer treatment would be most useful for patients. The available cancer treatments include systemic therapies, such as chemotherapy, targeted therapy, hormone therapy, immunotherapy, stem cell transplantation, and chimeric antigen receptor (CAR) T-Cell therapy. They also include regional therapies, such as radiation therapy; and local therapies, such as surgery.

The types of treatment that a cancer patient receives typically depends on the cancer itself and how advanced it is. Some people with cancer will have only one treatment, such as surgery for a local cancer, or regional therapy, for a regional cancer. But most people will have a combination of treatments, such as surgery with chemotherapy and/or radiation therapy.

Even with the most precise determination of types of treatments to use, the cancer in a patient may develop resistance to the selected treatment. There is a need for improved cancer treatments that have a broad-spectrum of activity against numerous types of cancer and there is a need for therapies that have activity against cancers that have been resistant to standard systemic therapies.

SUMMARY

The disclosure is directed to methods of treating cancer in a human subject comprising administering to the subject a regimen comprising sequential and/or concurrent administration of tamoxifen, gefitinib, and vinorelbine.

The disclosure is also directed to methods of treating cancer in a subject comprising administering to the subject a regimen of sequential and/or concurrent administration of tamoxifen, gefitinib, and a prescribed chemotherapeutic.

The disclosure is also directed to methods of treating cancer in a human subject comprising administering to the subject a regimen comprising sequential and/or concurrent administration of tamoxifen, gefitinib, and vinorelbine in metronomic dosing.

The disclosure is also directed to kits comprising tamoxifen and gefitinib, optionally, in a blister pack, each blister pack comprising a dose of tamoxifen and gefitinib for daily use. Other kits of the disclosure include those comprising tamoxifen, gefitinib, and vinorelbine.

DETAILED DESCRIPTION

The present disclosure may be understood more readily by reference to the following detailed description of desired embodiments and the examples included therein.

Throughout this text, the descriptions refer to methods of using anti-cancer therapeutics.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

Various terms relating to aspects of the description are used throughout the specification and claims. Such terms are to be given their ordinary meaning in the art unless otherwise indicated. Other specifically defined terms are to be construed in a manner consistent with the definitions provided herein.

"Substantial" refers to a degree of similarity, difference, increase, or decrease, as in a comparison to a known value. Substantial can include at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% similarity, difference, increase, or decrease, as in a comparison to a known value.

The terms "treating" or "treatment" refer to any success or indicia of success in the attenuation or amelioration of a cancer, including any objective or subjective parameter such as abatement, remission, diminishing of one or more symptoms of cancer, or making the injury, pathology, or condition more tolerable to the subject, improving the subject's physical well-being, or prolonging the length of survival. The treatment or amelioration of the one or more symptoms can be based on objective or subjective parameters; including the results of a physical examination, laboratory test(s), non-invasive imaging test(s), and/or self-reporting by the subject.

The terms "remission," "in remission from cancer," and "complete remission" refer to a state of improvement during a disease course, in which no physical, laboratory, imaging, and/or clinical evaluation identifies signs of the disease.

The term "partial remission" refers to a state of improvement during a disease course, in which physical, laboratory, imaging, and/or clinical evaluation identifies residual signs of the disease.

The terms "effective amount" and "therapeutically effective amount" are used interchangeably herein and refer to an amount of the drug effective to achieve a particular biological or therapeutic result such as, but not limited to, amelioration of one or more symptoms of cancer. A therapeutically effective amount of drug may vary according to factors such as the disease state, age, sex, body surface area, and body weight of the individual, and the ability of the drug to elicit a desired response in the individual. Such results may include, but are not limited to, the treatment of cancer, as determined by any means suitable in the art.

The term "subject" as used herein is intended to mean any animal, in particular, mammals. The methods described herein are applicable to human and nonhuman animals, although preferably used with pets and humans, and most preferably with humans. "Subject" and "patient" are used interchangeably herein. In some embodiments, the subject is human.

The term "metronomic dose" or "metronomic dosing" refers to a treatment in which comparatively low doses of anticancer drugs are given on a continuous or frequent, regular schedule (such as daily or weekly), usually chronically. Without wishing to be bound to any particular theory, chemotherapy with metronomic dosing according to the disclosure is effective and safe for the treatment of cancer.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. The materials, methods, and examples disclosed herein are illustrative only and not intended to be limiting.

It is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise. The term "about" as used herein when referring to a measurable value such as an amount, a temporal duration, and the like, is meant to encompass variations of ±10%, ±5%, ±1%, or ±0.1% from the specified value, as such variations are appropriate to perform the disclosed methods.

As used herein, approximating language may be applied to modify any quantitative representation that may vary without resulting in a change in the basic function to which it is related. Accordingly, a value modified by "about" may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints (e.g., "between 2 grams and 10 grams, and all the intermediate values includes 2 grams, 10 grams, and all intermediate values"). The endpoints of the ranges and any values disclosed herein are not limited to the precise range or value; they are sufficiently imprecise to include values approximating these ranges and/or values. All ranges are combinable.

Further, the term "comprising" should be understood as having its open-ended meaning of "including," but the term also includes the closed meaning of the term "consisting." For example, a composition that comprises components A and B may be a composition that includes A, B, and other components, but may also be a composition made of A and B only.

As used in this specification and the appended claims, the singular forms "a," "an," and "the" include plural referents unless the content clearly dictates otherwise. Thus, for example, reference to "a cell" includes a combination of two or more cells, and the like.

Triple-Agent Therapy for Treating Cancer

Disclosed are methods of treating cancer in a subject, preferably a human subject, comprising administering to the subject a regimen of sequential and/or concurrent administration of tamoxifen, gefitinib, and vinorelbine.

In some aspects of the disclosure, the tamoxifen, gefitinib, and vinorelbine are administered sequentially. For sequential administration, each dose of tamoxifen, gefitinib, and vinorelbine is administered at discrete time intervals from each administered dose, such as 30 min, one hour, two hours, three hours, four hours, five hours, six hours, seven hours, eight hours, nine hours, ten hours, 11 hours, 12 hours, or more hours apart. In other aspects, the tamoxifen, gefitinib, and vinorelbine are administered concurrently, such as without discrete time intervals from each administered dose. In yet other aspects, one or more of tamoxifen, gefitinib, and vinorelbine is administered sequentially or concurrently with the other of tamoxifen, gefitinib, and vinorelbine.

In some aspects, the methods comprise a regimen of administering tamoxifen and gefitinib concurrently twice daily, and vinorelbine once daily, for three days. The methods can comprise a regimen of administering tamoxifen and gefitinib concurrently twice daily for three consecutive days, and vinorelbine once daily on day 2 of the three consecutive days.

In some aspects, the regimen is a three-day regimen repeated about every week, about every two weeks, about every three weeks, about every four weeks, or less frequently.

The regimen can be a one-day regimen conducted over one day, over two consecutive days, over three consecutive days, over four consecutive days, over five consecutive days, over six consecutive days, over consecutive seven days, over eight consecutive days, over nine consecutive days, or over ten consecutive days. For example, the regimen may be a daily regimen. The regimen can also be continued over a period of months or years.

In some embodiments, gefitinib is administered at a dose of about 10-500 mg/m$^2$ per administration. For example, gefitinib can be administered at a dose of about 10-500 mg/m$^2$ per administration, at a dose of about 50-400 mg/m$^2$ per administration, at a dose of about 100-300 mg/m$^2$ per administration, or at a dose of about 100-200 mg/m$^2$ per administration. In other examples, gefitinib can be administered at a dose of about 10-300 mg/m$^2$ per administration, at a dose of about 10-200 mg/m$^2$ per administration, at a dose of about 10-190 mg/m$^2$ per administration, or at a dose of about 10-180 mg/m$^2$ per administration. In other examples, gefitinib can be administered at a dose of about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 187.5 mg/m$^2$, about 200 mg/m$^2$, about 225 mg/m$^2$, about 250 mg/m$^2$, about 275 mg/m$^2$, about 300 mg/m$^2$, about 325 mg/m$^2$, about 350 mg/m$^2$, about 375 mg/m$^2$, about 400 mg/m$^2$, about 425 mg/m$^2$, about 450 mg/m$^2$, about 475 mg/m$^2$, or about 500 mg/m$^2$ per administration.

In some embodiments, tamoxifen is administered at a dose of about 10-500 mg/m$^2$ per administration. For example, tamoxifen can be administered at a dose of about 10-500 mg/m$^2$ per administration, at a dose of about 10-400 mg/m$^2$ per administration, at a dose of about 10-300 mg/m$^2$ per administration, at a dose of about 10-200 mg/m$^2$ per administration, or at a dose of about 10-100 mg/m$^2$ per administration. In other examples, tamoxifen can be administered at a dose of about 10-90 mg/m$^2$ per administration, at a dose of about 10-80 mg/m$^2$ per administration, at a dose of about 10-70 mg/m$^2$ per administration, at a dose of about 10-60 mg/m$^2$ per administration, at a dose of about 10-50 mg/m$^2$ per administration, at a dose of about 10-40 mg/m$^2$ per administration, at a dose of about 10-30 mg/m$^2$ per administration, or at a dose of about 10-20 mg/m$^2$ per administration. In other examples, tamoxifen can be administered at a dose of about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 200 mg/m$^2$, about 225 mg/m$^2$, about 250 mg/m$^2$, about 275 mg/m$^2$, about 300 mg/m$^2$, about 325 mg/m$^2$, about 350 mg/m$^2$, about 375 mg/m$^2$, about 400 mg/m$^2$, about 425 mg/m$^2$, about 450 mg/m$^2$, about 475 mg/m$^2$, or about 500 mg/m$^2$ per administration.

In some embodiments, vinorelbine is administered at a dose of about 5-250 mg/m$^2$ per administration. For example, vinorelbine can be administered at a dose of about 50-250 mg/m$^2$ per administration, at a dose of about 50-200 mg/m$^2$ per administration, at a dose of about 50-150 mg/m$^2$ per administration, at a dose of about 50-100 mg/m$^2$ per administration, or at a dose of about 50-90 mg/m$^2$ per administration. In other examples, vinorelbine can be administered at a dose of about 5-100 mg/m$^2$ per administration, at a dose of about 5-90 mg/m$^2$ per administration, at a dose of about 5-80 mg/m$^2$ per administration, at a dose of about 5-70 mg/m$^2$ per administration, at a dose of about 5-60 mg/m$^2$ per administration, at a dose of about 5-50 mg/m$^2$ per administration, at a dose of about 5-40 mg/m$^2$ per administration, at a dose of about 5-30 mg/m$^2$ per administration, or at a dose of about 5-20 mg/m$^2$ per administration. In other examples, vinorelbine can be administered at a dose of about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 200 mg/m$^2$, about 225 mg/m$^2$, or about 250 mg/m$^2$ per administration.

In one embodiment, the regimen comprises orally administering between 150-225 mg/m$^2$ of gefitinib to the subject, twice daily, on days 1, 2, and 3 of the regimen, orally administering 64-96 mg/m$^2$ of tamoxifen to the subject, twice daily, on days 1, 2, and 3 of the regimen, and orally or intravenously administering an effective amount of vinorelbine to the subject on day 2 of the regimen.

In one embodiment, the regimen comprises orally administering between 150-225 mg/m$^2$ of gefitinib to the subject, twice daily, on days 1, 2, and 3 of the regimen, orally administering 64-96 mg/m$^2$ of tamoxifen to the subject, twice daily, on days 1, 2, and 3 of the regimen, and vinorelbine intravenously to the subject on day 2 of the regimen. In another embodiment, the regimen comprises orally administering between 150-225 mg/m$^2$ of gefitinib to the subject, twice daily, on days 1, 2, and 3 of the regimen, orally administering 64-96 mg/m$^2$ of tamoxifen to the subject, twice daily, on days 1, 2, and 3 of the regimen, and vinorelbine orally to the subject on day 2 of the regimen.

The methods of the disclosure can comprise administering between about 10 mg/m$^2$ and about 96 mg/m$^2$ of vinorelbine per administration to the subject on day 2 of the regimen.

The methods can further comprise administering about 187.5 mg/m$^2$ of gefitinib orally, twice daily, on days 1, 2, and 3 of the regimen.

The methods can further comprise administering about 80 mg/m$^2$ of tamoxifen orally, twice daily, on days 1, 2, and 3 of the regimen.

In some embodiments of the methods, about 80 mg/m$^2$ of vinorelbine is orally or intravenously administered on day 2 of the regimen. In some embodiments of the methods, about 30 mg/m$^2$ of vinorelbine is orally or intravenously administered on day 2 of the regimen.

Exemplary regimens with oral or intravenous vinorelbine are listed in Tables 1 and 2.

TABLE 1

Exemplary treatment regimen with oral dose units per m$^2$ surface area.

|  |  | First half of the day |  | Midday |  | Second half of the day |  |
| --- | --- | --- | --- | --- | --- | --- | --- |
|  | Drug | Oral Dose | Drug | Oral Dose | Drug | Oral Dose |
| Day 1 | tamoxifen | 80 mg/m$^2$ |  |  | tamoxifen | 80 mg/m$^2$ |
|  | gefitinib | 187.5 mg/m$^2$ |  |  | gefitinib | 187.5 mg/m$^2$ |
| Day 2 | tamoxifen | 80 mg/m$^2$ | vinorelbine | 80 mg/m$^2$ | tamoxifen | 80 mg/m$^2$ |
|  | gefitinib | 187.5 mg/m$^2$ |  |  | gefitinib | 187.5 mg/m$^2$ |
| Day 3 | tamoxifen | 80 mg/m$^2$ |  |  | tamoxifen | 80 mg/m$^2$ |
|  | gefitinib | 187.5 mg/m$^2$ |  |  | gefitinib | 187.5 mg/m$^2$ |

TABLE 2

| Exemplary treatment regimen with oral and injectable dose units per m² surface area. | | | | | | | |
|---|---|---|---|---|---|---|---|
| | | | | Midday | | | |
| | First half of the day | | | Injectable | Second half of the day | | |
| | Drug | Oral Dose | Drug | Dose | Drug | | Oral Dose |
| Day 1 | tamoxifen | 80 mg/m² | | | tamoxifen | | 80 mg/m² |
| | gefitinib | 187.5 mg/m² | | | gefitinib | | 187.5 mg/m² |
| Day 2 | tamoxifen | 80 mg/m² | vinorelbine | 30 mg/m² | tamoxifen | | 80 mg/m² |
| | gefitinib | 187.5 mg/m² | | | gefitinib | | 187.5 mg/m² |
| Day 3 | tamoxifen | 80 mg/m² | | | tamoxifen | | 80 mg/m² |
| | gefitinib | 187.5 mg/m² | | | gefitinib | | 187.5 mg/m² |

The subjects treated according to the disclosure can have a body surface area of between about 0.5 m² and about 3.6 m². In some embodiments, the subject has a surface area of about 0.243 m², about 0.563 m², about 0.787 m², about 1.236 m², about 1.603 m², about 1.92 m², about 1.98 m², about 2.06 m², about 2.5 m², about 3 m², or about 3.6 m².

In some embodiments of the methods, the doses for gefitinib, tamoxifen, and vinorelbine can be adjusted per subject, based on the subject's body surface area. In specific embodiments of the methods where gefitinib is administered orally at about 187.5 mg/m² per administration; tamoxifen is administered orally at about 80 mg/m² per administration; and vinorelbine is administered orally at about 80 mg/m² per administration, the dose per administration for each of tamoxifen, gefitinib, and vinorelbine can be adjusted per subject, based on the subject's body surface area, as indicated in Table 3.

TABLE 3

| Conversion table for dosage units per body surface area | | | | |
|---|---|---|---|---|
| Subject | Body Surface area (m²) | Dose per administration (mg) | | |
| | | tamoxifen | gefitinib | vinorelbine |
| Neonate (newborn) | 0.243 | 19.44 | 45.5625 | 19.44 |
| 2 years | 0.563 | 45.04 | 105.5625 | 45.04 |
| 5 years | 0.787 | 62.96 | 147.5625 | 62.96 |
| 10 years | 1.236 | 98.88 | 231.75 | 98.88 |
| 13 years | 1.603 | 128.24 | 300.5625 | 128.24 |
| 18 years | 1.98 | 158.4 | 371.25 | 158.4 |
| 20-79 years | 2.06 | 164.8 | 386.25 | 164.8 |
| 80+ years | 1.92 | 153.6 | 360 | 153.6 |
| Low limit | 0.2 | 16 | 37.5 | 16 |
| High limit | 3.6 | 288 | 675 | 288 |

Two-Drug Combination as an Adjuvant

Also disclosed are methods of treating cancer in a subject, preferably a human subject, comprising administering to the subject a regimen of sequential and/or concurrent administration of tamoxifen, gefitinib, and prescribed treatment to which the patient has become resistant. In these methods, the two-drug combination—tamoxifen and gefitinib (TG) combination—is used as an adjuvant. The TG combination enhances the effect of a prescribed treatment. The prescribed treatment can be a prescribed chemotherapeutic drug or a prescribed chemotherapeutic drug combination, to which the patient had developed resistance. With the addition of TG to the prescribed treatment, the patient is able to carry on the prescribed treatment even when the cancer has become non-responsive to the prescribed treatment.

In the methods comprising administering to the subject a regimen of sequential and/or concurrent administration of tamoxifen, gefitinib, and a prescribed treatment to which the patient has become resistant, the administration of TG can comprise a daily regimen of tamoxifen administered at a dose of about 10-500 mg/m² per administration, and a daily regimen of gefitinib administered at a dose of about 10-500 mg/m² per administration.

For example, administration of tamoxifen, gefitinib, and a prescribed treatment to which the patient has become resistant can comprise administering tamoxifen at a dose of about 10-500 mg/m² per administration, at a dose of about 10-400 mg/m² per administration, at a dose of about 10-300 mg/m² per administration, at a dose of about 10-200 mg/m² per administration, or at a dose of about 10-100 mg/m² per administration. In other examples, tamoxifen can be administered at a dose of about 10-90 mg/m² per administration, at a dose of about 10-80 mg/m² per administration, at a dose of about 10-70 mg/m² per administration, at a dose of about 10-60 mg/m² per administration, at a dose of about 10-50 mg/m² per administration, at a dose of about 10-40 mg/m² per administration, at a dose of about 10-30 mg/m² per administration, or at a dose of about 10-20 mg/m² per administration. In other examples, tamoxifen can be administered at a dose of about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 125 mg/m², about 150 mg/m², about 175 mg/m², about 200 mg/m², about 225 mg/m², about 250 mg/m², about 275 mg/m², about 300 mg/m², about 325 mg/m², about 350 mg/m², about 375 mg/m², about 400 mg/m², about 425 mg/m², about 450 mg/m², about 475 mg/m², or about 500 mg/m² per administration.

The administration of tamoxifen, gefitinib, and the prescribed treatment to which the patient has become resistant can comprise administering gefitinib at a dose of about 10-500 mg/m² per administration, at a dose of about 50-400 mg/m² per administration, at a dose of about 100-300 mg/m² per administration, or at a dose of about 100-200 mg/m² per administration. In other examples, gefitinib can be administered at a dose of about 10-300 mg/m² per administration, at a dose of about 10-200 mg/m² per administration, at a dose of about 10-190 mg/m² per administration, or at a dose of about 10-180 mg/m² per administration. In other examples, gefitinib can be administered at a dose of about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 125 mg/m², about 150 mg/m², about 175 mg/m², about 187.5 mg/m², about 200 mg/m², about 225 mg/m², about 250 mg/m², about 275 mg/m², about 300 mg/m², about 325 mg/m², about 350 mg/m², about 375 mg/m², about 400 mg/m², about 425 mg/m², about 450 mg/m², about 475 mg/m², or about 500 mg/m² per administration.

The disclosed methods can comprise the two-drug combination, TG combination, in use with vinorelbine and/or in use with a prescribed treatment. The prescribed treatment can comprise treatment with any one or a combination of chemotherapeutic drug(s) abiraterone acetate, albumin-bound (nab) paclitaxel, alemtuzumab, altretamine, belinostat, bendamustine, bevacizumab, blinatumomab, bleomycin, bortezomib, brentuximab vedotin, busulfan, cabazitaxel, capecitabine, carboplatin, carmustine, ceritinib, cetuximab, chlorambucil, cisplatin, cladribine, crizotinib, cyclophosphamide, cytarabine (Ara-C), dabrafenib, dacarbazine, dactinomycin, dasatinib, daunorubicin, DaunoXome (liposomal daunorubicin), DepoCyt (liposomal cytarabine), Doxil (liposomal doxorubicin), doxorubicin, epirubicin, eribulin mesylate, erlotinib, estramustine, etoposide, everolimus, floxuridine, fludarabine, gemcitabine, gliadel wafers, hydroxyurea, ibritumomab, ibrutinib, idarubicin, idelalisib, ifosfamide, imatinib, ipilimumab, irinotecan, ixabepilone, lanreotide, lapatinib, lenalidomide, lenvatinib, lomustine, mechlorethamine, melphalan, mercaptopurine, methotrexate, mitomycin, mitoxantrone, nilotinib, nivolumab, ofatumumab, olaparib, oxaliplatin, paclitaxel, palbociclib, panitumumab, pazopanib, panobinostat, PEG-asparaginase, peginterferon alfa-2b, pembrolizumab, pemetrexed, pentostatin, pralatrexate, procarbazine, ramucirumab, rituximab, romidepsin, sipuleucel-T, sorafenib, streptozocin, sunitinib, temozolomide, temsirolimus, teniposide, thalidomide, thioguanine, thiotepa, topotecan, tositumomab, trametinib, trastuzumab, valrubicin, vandetanib, vemurafenib, vinblastine, vincristine, and vinorelbine.

The disclosed methods can comprise the two-drug combination, TG combination, in use with a prescribed treatment, where the chemotherapeutic drug of the prescribed treatment is administered as per prescribed treatment regimen.

Cancers to be Treated

The methods can include repeating the regimen about every week, about every 2 weeks, about every 3 weeks, about every four weeks, or less frequently. The methods can include repeating the regimen in subjects with cancer or in subjects in remission from cancer. The cancer can be solid cancer or blood cancer. The cancer can be stage I cancer, stage II cancer, stage III cancer, or stage IV cancer. Suitable cancers include, but are not limited to, Acute Lymphoblastic Leukemia (ALL), Acute Myeloid Leukemia (AML), Adrenocortical Carcinoma Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Atypical Teratoid/Rhabdoid Tumor, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Carcinoid Tumor, Carcinoma of Unknown Primary, Cardiac Tumors, Medulloblastoma and Other CNS Embryonal Tumors, Germ Cell Tumor, Primary CNS Lymphoma, Cervical Cancer, Childhood Cancers, Cholangiocarcinoma, Chordoma, Childhood Bone Cancer, Chronic Lymphocytic Leukemia (CLL), Chronic Myelogenous Leukemia (CML), Chronic Myeloproliferative Neoplasms, Colorectal Cancer, Craniopharyngioma, Mycosis Fungoides and Sézary Syndrome, Ductal Carcinoma In Situ (DCIS), Embryonal Tumors, Medulloblastoma, Endometrial Cancer, Ependymoma, Esophageal Cancer, Esthesioneuroblastoma, Ewing Sarcoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Osteosarcoma, Gallbladder Cancer, Gastric (Stomach) Cancer, Gastrointestinal Carcinoid Tumor, Gastrointestinal Stromal Tumors, Germ Cell Tumors, Childhood Central Nervous System Germ Cell Tumors, Ovarian Germ Cell Tumors, Testicular Cancer, Gestational Trophoblastic Disease, Hairy Cell Leukemia, Head and Neck Cancer, Heart Tumors, Childhood, Hepatocellular (Liver) Cancer, Langerhans Cell Histiocytosis, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell, Small Cell, Pleuropulmonary Blastoma, and Tracheobronchial Tumor), Lymphoma, Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, Acute (AML), Chronic Myeloproliferative Neoplasms, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Undifferentiated Pleomorphic Sarcoma of Bone Treatment, Ovarian Cancer, Pancreatic Cancer, Pancreatic Neuroendocrine Tumors (Islet Cell Tumors), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma (Lung Cancer), Pregnancy and Breast Cancer, Primary Central Nervous System (CNS) Lymphoma, Primary Peritoneal Cancer, Prostate Cancer, Rare Cancers of Childhood, Rectal Cancer, Recurrent Cancer, Renal Cell (Kidney) Cancer, Retinoblastoma, Rhabdomyosarcoma (Childhood Soft Tissue Sarcoma), Salivary Gland Cancer (Head and Neck Cancer), Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sézary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, Cutaneous T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Tracheobronchial Tumors (Lung Cancer), Transitional Cell Cancer of the Renal Pelvis and Ureter (Kidney (Renal Cell) Cancer), Carcinoma of Unknown Primary, Ureter and Renal Pelvis, Transitional Cell Cancer (Kidney (Renal Cell) Cancer, Urethral Cancer, Endometrial Uterine Cancer, Uterine Sarcoma, Vaginal Cancer, Vascular Tumors, Vulvar Cancer, and Wilms Tumor and Other Childhood Kidney Tumors.

In some embodiments, the cancer is breast cancer, bowel (colon) cancer, pancreatic cancer, esophageal cancer, skin (melanoma and squamous cell) cancer, prostate cancer, neuroendocrine cancer, lung (small and large cell) cancer, brain (GBM) cancer, acute myelogenous leukemia, non-Hodgkins lymphoma, or meningeal cancer.

The disclosed methods can result in a reduction in the size of the cancer tumor, as compared to the size of the cancer tumor prior to applying the methods in the same subjects. The reduction in the size of the cancer tumor can be a substantial reduction, such as a reduction by at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% relative to the size of the cancer tumor prior to applying the disclosed methods to the subject.

In some aspects, the disclosed methods can result in a decrease in the level of a circulating cancer marker(s), as compared to the level of circulating cancer marker(s) prior to the method. The decrease in the level of a circulating cancer marker(s) can be a substantial decrease, such as a decrease by at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% relative to the level of the circulating cancer marker(s) prior to applying the disclosed methods to the subject. The methods can results in an improvement in the subject's Anamnestic Comparative Self Assessment (ACSA), as compared to the subject's ACSA prior to the method.

Also disclosed are methods for in vitro testing a drug combination on cancer cells of a subject for cancer cell survival, wherein the drug combination comprises tamoxifen, gefitinib, and vinorelbine. The in vitro testing can comprise administering tamoxifen and gefitinib prior to, together with, and/or after, administering vinorelbine. The in vitro testing can comprise measuring the cancer cell survival. Suitable in vitro tests and methods for measuring the cancer cell survival include Differential Staining Cytotoxicity Assay (DiSC), MTT assay, ATP assay, and fluorescein diacetate assay (FDA). MTT assay is a colorimetric assay for assessing cell metabolic activity. Cellular enzymes are capable of reducing the tetrazolium dye MTT 3-(4,5-dimethylthiazol-2-yl)-2,5-diphenyltetrazolium bromide to its insoluble formazan, which has a purple color. ATP assays are procedures that can measure cell viability based on detection of ATP. All living cells, including bacteria, can be detected with ATP assays. Several detection methods can be used, such as colorimetric, fluorescent and bioluminescent. FDA uses a cell-permeant esterase substrate fluorescein diacetate that can serve as a viability probe and that measures both enzymatic activity, which is required to activate its fluorescence, and cell-membrane integrity, which is required for intracellular retention of their fluorescent product.

The in vitro testing can provide a substantial reduction in the cancer cell survival of cells obtained from the subject with the drug combination. The substantial reduction in cancer cell survival with the drug combination can be a reduction by between about 50% and about 100% relative to the cancer cell survival in the absence of the drug combination. The substantial reduction in cancer cell survival can be a reduction by at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% relative to the cancer cell survival in the absence of the drug combination.

Also disclosed are methods of treating cancer in a subject comprising first in vitro testing a drug combination on cancer cells of the subject for cancer cell survival, wherein the drug combination comprises tamoxifen, gefitinib, and vinorelbine; and then administering to the subject any of the disclosed treatment regimens.

Use of the Three-Drug Tamoxifen, Gefitinib, and Vinorelbine (TGV) Regimen

Tamoxifen is used and approved for the temporary non curative management of breast cancer. Gefitinib is used for the temporary non curative treatment of EGFR-positive non-small cell lung cancer. Vinorelbine is used for the palliative therapy (temporary and noncurative treatment) of two types of human cancer, non-small cell lung cancer and breast cancer.

Disclosed are treatment regimens of a combination of all these three medications, tamoxifen, gefitinib, and vinorelbine. The treatment regimen demonstrates remissions in a broad spectrum of human cancers. The three-drug TGV combination shows remissions in cancers that have spread to or started inside the blood-brain barrier. This is an extremely rare observation in cancer therapy. TGV has applications well beyond the limited cancers for which each of these drugs has been approved individually. None of tamoxifen, gefitinib, and vinorelbine have demonstrated therapeutic effectiveness inside the blood-brain barrier, where surgery or radiation are the sole means of therapeutic intervention.

The disclosed treatment regimen uses a combination of tamoxifen, gefitinib, and/or vinorelbine, at a broad range of doses per administration (from subtherapeutic to several times over Food and Drug Administration approved therapeutic doses) per treatment. Tamoxifen can be used at nearly eight times the therapeutic dose of its standard dose and gefitinib at twice the standard dose.

The three drugs can be used at or above their respective approved therapeutic doses. Their use according to the disclosed regimens does not result in toxicities greater than what would be expected with the respective approved therapeutic doses. The worst toxicities of chemotherapy at approved therapeutic doses include nausea, vomiting, hair loss, loss of nailbeds, rash, life threatening neutropenia, thrombocytopenia, anemia, and neuropathy. The disclosed regimens have substantially reduced toxicities relative to the worst toxicities of chemotherapy at approved therapeutic doses. The described regimens have low toxicity characterized with no substantial nausea, no substantial vomiting, no substantial hair loss, no substantial loss of nailbeds, no substantial rash, no substantial life threatening neutropenia, no substantial thrombocytopenia, minimal anemia, and/or minimal neuropathy relative to the worst toxicities of chemotherapy at approved therapeutic doses.

While not wishing to be bound to any particularly theory, the two drugs, tamoxifen and gefitinib, used in relatively high concentrations, may accelerate the transport of the third drug (e.g., vinorelbine) into the cancer cell almost exclusively, and/or may prevent egress of the third drug (e.g., vinorelbine). Because of this cancer-specific transfer of vinorelbine, and/or cancer-specific retention of vinorelbine, the therapeutic toxicities from the combination of all three drugs are mild, e.g., mild myelosuppression, occasional diarrhea, which is usually followed by mild constipation, both of which are easily managed with over-the-counter antidiarrheals and laxatives.

The described concentration of two of the three generic drugs affect the unique synergy of the three together. This allows the regimen to have broad-spectrum application of this combination of three generic drugs in the many cancers observed to have responded to the disclosed triple therapy. As the examples demonstrate, remissions have been seen in metastatic squamous cell carcinoma of the skin, metastatic breast cancer, metastatic prostate cancer, glioblastoma multiforme (GBM) and leptomeningeal breast cancer inside the blood-brain barrier, metastatic pancreatic cancer, non-small cell lung cancer, small cell lung cancer, and many other cancers.

The three drugs can be administered orally. The three drugs can be provided in a blister pack of pills given over 3 days. The dose of the three drugs can be adjusted for the body surface area of the patients who will administer the medication to themselves. The frequency of administration of the regimen may be once, once every week, once every two weeks, once every three weeks, once every four weeks, or less frequently.

In one embodiment, tamoxifen and gefitinib can be given at a certain concentration in six pills, which can be given twice a day on the day before, twice a day on the day of, and twice a day on the day after the administration of oral vinorelbine. In some aspects, vinorelbine can be a seventh pill administered in the middle of the day on day two of the three-day treatment. In one embodiments, a patient with a body surface area of 1.5 meter squared can be given a blister pack of five pills, which can be taken twice a day on the day before, twice a day on the day of, and twice a day on the day after the administration of five pills of vinorelbine, the latter given in the middle of day two. In one embodiment, a patient with a body surface area of 1.75 meter squared can take a combination of six pills twice a day on the day before, twice a day on the day of and twice a day on the day after taking six pills of vinorelbine. So as the body surface area increases, the number of pills increases in proportion.

Metronomic Treatment

According to the conventional chemotherapy regimens, anticancer drugs are administered in cycles near or at the maximum tolerated dose (MDT) and they alternate with long drug-free period to allow the patient to recover from adverse drug reactions. This strategy is successful in controlling the disease process in a significant number of patients (both adult and pediatric).

The main characteristics of metronomic chemotherapy, as opposed to conventional chemotherapy regimens, (as described in Mross et al., *J Cancer Ther Res.* 2012; 1:32; Maiiti, *J Pharmacol Pharmacother.* 2014 July-September; 5 (3): 186-192) are:

Frequent (dose-dense) administration of chemotherapy without any significant interruptions;

Using a biological optimized dose instead of MTD;

No application of hematopoietic growth factors;

Preference for oral drugs;

Low incidence of treatment related side-effects; and

Potential for delayed development of resistance.

Disclosed are methods of treating cancer in a subject comprising administering to the subject a regimen comprising sequential and/or concurrent administration of tamoxifen, gefitinib, and vinorelbine in a metronomic dosing regimen. The metronomic dosing regimen can comprise administering tamoxifen at a dose of 5-500 mg/m$^2$ per administration, gefitinib at a dose of 5-500 mg/m$^2$ per administration, and vinorelbine at a dose of 5-500 mg/m$^2$ per administration.

The metronomic treatment can include administering tamoxifen at a dose of about 5-500 mg/m$^2$ per administration. For example, metronomic treatment can include administering tamoxifen at a dose of about 5-500 mg/m$^2$ per administration, at a dose of about 5-400 mg/m$^2$ per administration, at a dose of about 5-300 mg/m$^2$ per administration, at a dose of about 5-200 mg/m$^2$ per administration, at a dose of about 5-175 mg/m$^2$ per administration, at a dose of about 5-150 mg/m$^2$ per administration, at a dose of about 5-125 mg/m$^2$ per administration, or at a dose of about 5-100 mg/m$^2$ per administration. In other examples, metronomic treatment can include administering tamoxifen at a dose of about 5-100 mg/m$^2$ per administration, at a dose of about 5-90 mg/m$^2$ per administration, at a dose of about 5-80 mg/m$^2$ per administration, at a dose of about 5-70 mg/m$^2$ per administration, at a dose of about 5-60 mg/m$^2$ per administration, or at a dose of about 5-50 mg/m$^2$ per administration. In other examples, metronomic treatment can include administering tamoxifen at a dose of about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 200 mg/m$^2$, about 300 mg/m$^2$, about 400 mg/m$^2$, or about 500 mg/m$^2$ per administration.

The metronomic treatment can include administering gefitinib at a dose of about 5-500 mg/m$^2$ per administration. For example, metronomic treatment can include administering gefitinib at a dose of about 5-500 mg/m$^2$ per administration, at a dose of about 5-400 mg/m$^2$ per administration, at a dose of about 5-300 mg/m$^2$ per administration, at a dose of about 5-200 per administration, at a dose of about 5-175 mg/m$^2$ per administration, at a dose of about 5-150 mg/m$^2$ per administration, at a dose of about 5-125 mg/m$^2$ per administration, or at a dose of about 5-100 mg/m$^2$ per administration. In other examples, metronomic treatment can include administering gefitinib at a dose of about 5-100 mg/m$^2$ per administration, at a dose of about 5-90 mg/m$^2$ per administration, at a dose of about 5-80 mg/m$^2$ per administration, at a dose of about 5-70 mg/m$^2$ per administration, at a dose of about 5-60 mg/m$^2$ per administration, or at a dose of about 5-50 mg/m$^2$ per administration. In other examples, metronomic treatment can include administering gefitinib at a dose of about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 200 mg/m$^2$, about 300 mg/m$^2$, about 400 mg/m$^2$, or about 500 mg/m$^2$ per administration.

The metronomic treatment can include administering vinorelbine at a dose of about 5-500 mg/m$^2$ per administration. For example, metronomic treatment can include administering vinorelbine at a dose of about 5-500 mg/m$^2$ per administration, at a dose of about 5-400 mg/m$^2$ per administration, at a dose of about 5-300 mg/m$^2$ per administration, at a dose of about 5-200 mg/m$^2$ per administration, at a dose of about 5-175 mg/m$^2$ per administration, at a dose of about 5-150 mg/m$^2$ per administration, at a dose of about 5-125 mg/m$^2$ per administration, or at a dose of about 5-100 mg/m$^2$ per administration. In other examples, metronomic treatment can include administering vinorelbine at a dose of about 5-100 mg/m$^2$ per administration, at a dose of about 5-90 mg/m$^2$ per administration, at a dose of about 5-80 mg/m$^2$ per administration, at a dose of about 5-70 mg/m$^2$ per administration, at a dose of about 5-60 mg/m$^2$ per administration, or at a dose of about 5-50 mg/m$^2$ per administration. In other examples, metronomic treatment can include administering vinorelbine at a dose of about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 200 mg/m$^2$, about 300 mg/m$^2$, about 400 mg/m$^2$, or about 500 mg/m$^2$ per administration.

The metronomic dosing regimen can comprise administering the drugs sequentially and/or concurrently for a period of one day, two days, three days, four days, five days, six days, or seven days and can be repeated every week, every two weeks, every three weeks, every four weeks, or less frequently. The metronomic dosing regimen can comprise administering the drugs sequentially and/or concurrently over one day, over two consecutive days, over three consecutive days, over four consecutive days, over five consecutive days, over six consecutive days, over consecutive seven days, over eight consecutive days, over nine consecutive days, or over ten consecutive days for a period of months or years.

The metronomic treatment with the metronomic dosing regimen can be preceded with the triple-agent therapy.

Kits

Also disclosed are kits comprising tamoxifen, gefitinib, and vinorelbine. The kits can comprise tamoxifen and gefitinib, optionally, in a blister pack, each blister pack comprising a dose of tamoxifen and gefitinib for daily use. The kits can comprise tamoxifen, gefitinib, and vinorelbine, optionally, in a blister pack, each blister pack comprising a dose of tamoxifen, gefitinib, and vinorelbine for daily use.

The kits can comprise gefitinib in solid unit dosage forms of about 10-100 mg. The kits can comprise gefitinib in solid unit dosage forms of about 37.5 mg. The kits can comprise tamoxifen in solid unit dosage forms of about 10-30 mg. The kits can comprise tamoxifen in solid unit dosage forms of about 20 mg. The kits can comprise tamoxifen and gefitinib in a single dosage form. The kits can comprise tamoxifen and gefitinib in a single dosage form comprising about 20 mg tamoxifen and about 37.5 mg gefitinib. The kits can also comprise vinorelbine in liquid unit dosage forms of about 5-60 mg. The kits can also comprise vinorelbine in solid unit dosage forms of about 5-60 mg. The kits can be provided with instructions for use. Exemplary dosage units provided in the kits can include the dosage units listed in Table 4.

prescribed dose. The kit for oral administration of vinorelbine can provide vinorelbine in 20 mg capsules or in 30 mg capsules. The kit for intravenous administration of vinorelbine can provide 10 mg/ml of vinorelbine that can be administered at a doctor's office, at 30 mg per m$^2$, intravenously. For example, a blister pack for an exemplary treatment regimen as shown in Table 1 or Table 2 may include several rows of tamoxifen dosage units, several rows of gefitinib dosage units, or several rows of tamoxifen/gefitinib combined dosage units for days 1, 2 and 3 of the treatment regimen. The blister pack may also include one or more rows of vinorelbine dosage units for day 2 of the treatment regimen. Twice a day at days 1, 2, and 3 of the regimen, the patient can take several tamoxifen and gefitinib dosage units as needed as per prescribed dose. At midday of day two, the patient can take several vinorelbine capsules as needed per dose.

It is to be understood that the embodiments described herein are not limited to particular methods, reagents, compounds, compositions or biological systems, which can, of course, vary. It is also to be understood that the terminology used herein is for the purpose of describing the antibodies and antigen-binding fragments thereof, and methods of detecting and/or diagnosing and/or treating, and is not intended to be limiting.

ILLUSTRATIVE EMBODIMENTS

Embodiment 1. A method of treating cancer in a human subject comprising administering to the subject a regimen comprising sequential and/or concurrent administration of tamoxifen, gefitinib, and vinorelbine.

Embodiment 2. The method of embodiment 1, wherein the regimen comprises administering tamoxifen and gefitinib concurrently twice daily, and vinorelbine once daily, for three days.

Embodiment 3. The method of embodiment 1, wherein the regimen comprises administering tamoxifen and gefitinib concurrently twice daily for three consecutive days, and vinorelbine once daily on day 2 of the three consecutive days.

Embodiment 4. The method of any one of the preceding embodiments, wherein the regimen is repeated every week, every two weeks, every three weeks, every four weeks, or less frequently.

Embodiment 5. The method of any one of the preceding embodiments, wherein gefitinib is administered at a dose of 10-500 mg/m$^2$ per administration.

Embodiment 6. The method of any one of the preceding embodiments, wherein tamoxifen is administered at a dose of 10-500 mg/m$^2$ per administration.

TABLE 4

| | | | | tamoxifen/gefitinib |
| Dosage units for the kits. | | | | |
| | tamoxifen | gefitinib | vinorelbine | combined unit |
| --- | --- | --- | --- | --- |
| Oral dosage units Injectable dosage units | 10 mg tablet 20 mg tablet | 250 mg tablet | 20 mg capsule, liquid filled 30 mg capsule, liquid filled 10 mg/ml | 20 mg/37.5 mg tablet |

The kit components can provide the patient with the ability to self-administer the prescribed dose by providing several tamoxifen and gefitinib tablets as needed as per Embodiment 7. The method of any one of the preceding embodiments, wherein vinorelbine is administered at a dose of 5-250 mg/m$^2$ per administration.

Embodiment 8. The method of any one of the preceding embodiments, wherein the regimen is conducted over one day, over two consecutive days, over three consecutive days, over four consecutive days, over five consecutive days, over six consecutive days, over consecutive seven days, over eight consecutive days, over nine consecutive days, or over ten consecutive days.

Embodiment 9. The method of any one of preceding embodiments, wherein the regimen comprises orally administering between 150-225 mg/m² of gefitinib to the subject, twice daily, on days 1, 2, and 3 of the regimen, orally administering 64-96 mg/m² of tamoxifen to the subject, twice daily, on days 1, 2, and 3 of the regimen, and orally or intravenously administering an effective amount of vinorelbine to the subject on day 2 of the regimen.

Embodiment 10. The method any one of the preceding embodiments, wherein the vinorelbine is intravenously administered to the subject on day 2 of the regimen.

Embodiment 11. The method any one of the preceding embodiments, wherein the vinorelbine is orally administered to the subject on day 2 of the regimen.

Embodiment 12. The method any one of the preceding embodiments, wherein 10-96 mg/m² of vinorelbine is administered to the subject on day 2 of the regimen.

Embodiment 13. The method of any one of the preceding embodiments, wherein 187.5 mg/m² of gefitinib is orally administered twice daily, on days 1, 2, and 3 of the regimen.

Embodiment 14. The method of any one of the preceding embodiments, wherein 80 mg/m² of tamoxifen is orally administered twice daily, on days 1, 2, and 3 of the regimen.

Embodiment 15. The method of any one of the preceding embodiments, wherein 80 mg/m² of vinorelbine is orally or intravenously administered on day 2 of the regimen.

Embodiment 16. The method of any one of the preceding embodiments, wherein 30 mg/m² of vinorelbine is orally or intravenously administered on day 2 of the regimen.

Embodiment 17. A. method of treating cancer in a subject comprising administering to the subject a regimen of sequential and/or concurrent administration of tamoxifen, gefitinib, and a prescribed chemotherapeutic.

Embodiment 18. The method of embodiment 17, wherein tamoxifen is administered at a dose of 10-500 mg/m² per administration, gefitinib is administered at a dose of 10-500 mg/m² per administration, and the prescribed chemotherapeutic is administered at a prescribed dose.

Embodiment 19. The method of embodiment 17 or 18, wherein the prescribed chemotherapeutic is a chemotherapeutic to which the patient has become resistant.

Embodiment 20. The method of any one of the preceding embodiments, wherein the subject has a body surface area of 0.5 to 3.6 m².

Embodiment 21. The method of any one of the preceding embodiments, wherein the regimen is repeated about every 2 weeks.

Embodiment 22. The method of any one of the preceding embodiments, wherein the regimen is repeated about every 3 weeks.

Embodiment 23. The method of any one of the preceding embodiments, wherein the cancer is solid cancer or blood cancer.

Embodiment 24. The method of any one of the preceding embodiments, wherein the cancer is stage I cancer, stage II cancer, stage III cancer, or stage IV cancer.

Embodiment 25. The method of any one of the preceding embodiments, wherein the cancer is selected from the group consisting of Acute Lymphoblastic Leukemia (ALL), Acute Myeloid Leukemia (AML), Adrenocortical Carcinoma Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Atypical Teratoid/Rhabdoid Tumor, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Carcinoid Tumor, Carcinoma of Unknown Primary, Cardiac Tumors, Medulloblastoma and Other CNS Embryonal Tumors, Germ Cell Tumor, Primary CNS Lymphoma, Cervical Cancer, Childhood Cancers, Cholangiocarcinoma, Chordoma, Childhood Bone Cancer, Chronic Lymphocytic Leukemia (CLL), Chronic Myelogenous Leukemia (CML), Chronic Myeloproliferative Neoplasms, Colorectal Cancer, Craniopharyngioma, Mycosis Fungoides and Sézary Syndrome, Ductal Carcinoma In Situ (DCIS), Embryonal Tumors, Medulloblastoma, Endometrial Cancer, Ependymoma, Esophageal Cancer, Esthesioneuroblastoma, Ewing Sarcoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Osteosarcoma, Gallbladder Cancer, Gastric (Stomach) Cancer, Gastrointestinal Carcinoid Tumor, Gastrointestinal Stromal Tumors, Germ Cell Tumors, Childhood Central Nervous System Germ Cell Tumors, Ovarian Germ Cell Tumors, Testicular Cancer, Gestational Trophoblastic Disease, Hairy Cell Leukemia, Head and Neck Cancer, Heart Tumors, Childhood, Hepatocellular (Liver) Cancer, Langerhans Cell Histiocytosis, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell, Small Cell, Pleuropulmonary Blastoma, and Tracheobronchial Tumor), Lymphoma, Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, Acute (AML), Chronic Myeloproliferative Neoplasms, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Undifferentiated Pleomorphic Sarcoma of Bone Treatment, Ovarian Cancer, Pancreatic Cancer, Pancreatic Neuroendocrine Tumors (Islet Cell Tumors), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma (Lung Cancer), Pregnancy and Breast Cancer, Primary Central Nervous System (CNS) Lymphoma, Primary Peritoneal Cancer, Prostate Cancer, Rare Cancers of Childhood, Rectal Cancer, Recurrent Cancer, Renal Cell (Kidney) Cancer, Retinoblastoma, Rhabdomyosarcoma (Childhood Soft Tissue Sarcoma), Salivary Gland Cancer (Head and Neck Cancer), Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sézary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, Cutaneous T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Tracheobronchial Tumors (Lung Cancer), Transitional Cell Cancer of the Renal Pelvis and Ureter (Kidney (Renal Cell) Cancer), Carcinoma of Unknown Primary, Ureter and Renal Pelvis, Transitional Cell Cancer (Kidney (Renal Cell) Cancer, Urethral Cancer, Endometrial Uterine Cancer, Uterine Sarcoma, Vaginal Cancer, Vascular Tumors, Vulvar Cancer, and Wilms Tumor and Other Childhood Kidney Tumors.

Embodiment 26. The method of any one of the preceding embodiments, wherein the cancer is selected from the group consisting of breast cancer, bowel (colon) cancer, pancreatic cancer, esophageal cancer, skin (melanoma and squamous cell) cancer, prostate cancer, neuroendocrine cancer, lung (small and large cell) cancer, brain (GBM) cancer, acute myelogenous leukemia, non-Hodgkins lymphoma, and meningeal cancer.

Embodiment 27. The method of any one of the preceding embodiments, wherein the method results in a reduction in the size of the cancer tumor, as compared to the size of the cancer tumor prior to the method.

Embodiment 28. The method of any one of the preceding embodiments, wherein the method results in a decrease in the level of a circulating cancer marker(s), as compared to the level of circulating cancer marker(s) prior to the method.

Embodiment 29. The method of any one of the preceding embodiments, wherein the method results in an improvement in the subject's Anamnestic Comparative Self Assessment (ACSA), as compared to the subject's ACSA prior to the method.

Embodiment 30. A method of treating cancer in a human subject comprising administering to the subject a regimen comprising sequential and/or concurrent administration of tamoxifen, gefitinib, and vinorelbine in metronomic dosing.

Embodiment 31. The method of embodiment 30, wherein the regimen comprises administering tamoxifen at a dose of 5-500 mg/m$^2$ per administration, gefitinib administered at a dose of 5-500 mg/m$^2$ per administration, and vinorelbine administered at a dose of 5-500 mg/m$^2$ per administration.

Embodiment 32. The method of embodiment 30 or 31, wherein the regimen is administered for a period of months or years, optionally, after a method of treating cancer according to any one of embodiments 1-31.

Embodiment 33. A kit comprising tamoxifen and gefitinib, optionally, in a blister pack, each blister pack comprising a dose of tamoxifen and gefitinib for daily use.

Embodiment 34. A kit comprising tamoxifen, gefitinib, and vinorelbine.

Embodiment 35. The kit of embodiment 33 or 34, wherein the gefitinib is provided in solid unit dosage forms of about 5-500 mg.

Embodiment 36. The kit of any one of embodiments 33-35, wherein the gefitinib is provided in solid unit dosage forms of about 37.5 mg.

Embodiment 37. The kit of any one of embodiments 33-36, wherein the tamoxifen is provided in solid unit dosage forms of about 5-500 mg.

Embodiment 38. The kit of any one of embodiments 33-37, wherein the tamoxifen is provided in solid unit dosage forms of about 20 mg.

Embodiment 39. The kit of any one of embodiments 33-36, wherein the tamoxifen and the gefitinib are provided in a single dosage form.

Embodiment 40. The kit of any one of embodiments 33-39, wherein the tamoxifen and the gefitinib are provided in a single dosage form comprising about 20 mg tamoxifen and about 37.5 mg gefitinib.

Embodiment 41. The kit of any one of embodiments 33-40, wherein the vinorelbine is provided in liquid unit dosage forms of about 5-500 mg.

Embodiment 42. The kit of any one of embodiments 33-41, wherein the vinorelbine is provided in solid unit dosage forms of about 5-500 mg.

Embodiment 43. A method comprising in vitro testing a drug combination on cancer cells of a subject for cancer cell survival, wherein the drug combination comprises tamoxifen, gefitinib, and vinorelbine.

Embodiment 44. The method of embodiment 43, wherein in vitro testing comprises administering tamoxifen and gefitinib prior to, together with, and/or after, administering vinorelbine.

Embodiment 45. The method of embodiment 43 or 44, wherein in vitro testing comprises measuring the cancer cell survival.

Embodiment 46. The method of any one of embodiments 43-45, further comprising treating cancer in a subject according to any one of embodiments 1-16 and 20-32, when the in vitro testing provides substantial reduction in the cancer cell survival of cells obtained from the subject.

Embodiment 47. The method of embodiment 46, wherein substantial reduction in the cancer cell survival comprises between 50% and 100% reduction in the cancer cell survival.

Embodiment 48. A method of treating cancer in a subject comprising testing a drug combination on cancer cells of the subject for cancer cell survival, wherein the drug combination comprises tamoxifen, gefitinib, and vinorelbine; and administering to the subject the method of any one of embodiments 1-16 and 20-32.

EXAMPLES

An exemplary embodiment of a treatment regimen with TGV includes tamoxifen 80 milligrams per meter squared given orally twice daily for three days; gefitinib 187.5 mg per meters squared given orally twice daily for three days; and vinorelbine 80 mg per meter squared taken orally midday on day two of the three-day cycle.

Gefitinib at a dose of 37.5 mg and tamoxifen at a dose of 20 mg can be combined into a pill or capsule so that patients of various body surface areas can ingest, for example, five pills twice a day for three days if they were 1.2 to 1.3 meters squared in size; six pills twice a day if they were 1.4 to 1.6 meters squared; seven pills a day if they were 1.7 to 1.8 meters squared; and eight pills if they were 1.9 to 2.1 meters squared, and so on.

A blister pack may be prescribed so that the patient could easily measure the appropriate dose for each three-day cycle and the medications would be sequenced on the blister pack so that patients could easily self-administer the appropriate dose.

Use of tamoxifen at a high dose of 80 milligrams per meter squared (the typical dose in conventional cancer treatment is 20 mg daily) and high dose of gefitinib (187 milligrams per meter squared twice daily for 3 days—the typical dose in conventional cancer treatment is 250 mg daily) has been found in cytometric testing using live cancer cell cultures to transport vinorelbine into the cancer cell, producing extraordinary synergy in causing programmed apoptosis in the cancer cells (programmed cancer cell death) while sparing much of the normal tissues and giving dramatic clinical outcomes.

The treatment regimen with TGV has been found to cross the blood-brain barrier as it appears to have excellent clinical activity in primary brain cancer as a third or fourth-line drug therapy and on brain metastases from lung and breast cancers, including leptomeningeal breast cancer.

There is a broad spectrum of activity that extends from the more common breast, bowel, and lung cancers, and extends to pancreatic cancer, gastric cancer, metastatic squamous cell carcinoma of the skin, melanoma, neuroblastoma, cancer of the urachus, and many other cancers. A very high percentage of all these cancers respond to this regimen, showing the broad applicability of the triple-agent treatment regimen in cancer treatment. About 48% of all cancer cases are breast, lung, colon, pancreas, and prostate cancers. About 89% of these cases are adenocarcinomas. In the experimental studies, it was found that approximately 36% of all adenocarcinomas from any primary site were responsive in vitro and that about 33% of all adenocarcinomas would respond in vivo. Triple negative breast cancer, however, was a standout. Eighty percent of all cases of this notoriously refractory disease responded in vivo.

When tested in vitro, 94% of cancers that were predicted by the in vitro test to respond to TGV actually responded in vivo.

Below are 17 case studies of 17 cancer patients who have benefited from the TGV therapy. The treatment regimen for the TGV therapy is described in Tables 1 and 2. The 17 case studies represent patients with metastatic esophageal cancer, metastatic skin cancer, metastatic breast cancer, leptomeningeal breast cancer, metastatic prostate cancer, glioblastoma multiforme, lung cancer, bowel cancer, acute myelogenous leukemia, esthesioneuroblastoma, and urothelial cancer. The case studies demonstrate the TGV therapy has had a broad spectrum of application in different cancers with outstanding efficacy. The TGV therapy also had outstanding efficacy when given to patients who were previously heavily pre-treated for cancer. The TGV therapy was remarkably tolerable for patients, with extremely low toxicity.

Example 18 demonstrates the use of a two-drug combination—tamoxifen and gefitinib—as an adjuvant. The TG combination enhanced the effect of a chemotherapeutic drug combination to which the patient had developed resistance. With the addition of TG to the prescribed treatment, the patient was able to carry on with the prescribed treatment, a chemotherapeutic drug combination, and was responsive to this treatment.

Example 1. TGV Therapy for Metastatic Esophageal Cancer

The patient, a 66-year-old woman, developed an inability to swallow solid foods. After an upper endoscopy demonstrated adenocarcinoma of the esophagus, the patient was referred to a cancer treatment facility, which found extensive liver, bone, lung, and other metastases, and liver failure. She was told that she was not a candidate for any treatment.

Following a PET-CT scan, she was also told that she was not a candidate for any treatment. She later received the same response from a second treatment facility. Desperate this, the patient was admitted to receive the TGV therapy. A stent was placed in her esophagus. Tumor specimen was harvested from her liver for analysis.

The patient was given intrahepatic artery chemotherapy for the liver disease. After two weeks, liver function returned to normal but the remaining disease continued to grow. The patient was then put on the TGV regimen, which brought on a complete remission. The patient is alive and disease free six years after TGV treatment.

Example 2. TGV Therapy for Skin Cancer (Squamous Cell Carcinoma)

The patient, a 71-year-old male, developed a skin cancer (squamous cell carcinoma). The carcinoma was resected, but then reoccurred on the patient's scalp, developing rapidly into an $850 \text{ cm}^3$ mass. This metastasized to the lymph nodes in the chest and retroperitoneum.

A tissue biopsy was performed and sent for cytometric testing. The test showed that only TGV therapy would be active in his disease. The patient was started on TGV, went into complete remission, and is alive, and completely disease free four years after TGV treatment according to the disclosure.

Example 3. TGV Therapy for Breast Cancer Metastasized to the Brain

The patient is a 65-year-old woman, who was treated successfully for breast cancer, but who developed headaches twelve years later.

An MRI showed 31 metastases to her brain and widely metastatic disease in the lungs, bone, and liver. Neurosurgeons removed three of the 31 lesions in the cerebellum, which were sent for cytometric testing. The test showed TGV therapy would be active. The TGV therapy was administered for over six months. She went into complete remission. She is alive and disease free four years after TGV treatment according to the disclosure. No radiation, which is the standard treatment for this disease, was used during the treatment.

Example 4. TGV Therapy for Glioblastoma Multiforme

The patient is a 53-year-old woman with a multi-year history of resections of recurrent glioblastoma multiforme (GBM). She was treated with the standard therapy for GBM, which is radiation and Temodar® (Schering Corporation, Kenilworth, NJ), but the disease progressed, and she failed experimental regimens that left her wheelchair bound and her left arm paralyzed. She was sent to a neurosurgical unit for TGV therapy. She was started on the TGV regimen, and she is presently without any symptoms of her disease-she is no longer in a wheelchair, has recovered use of her left arm, and is in a near complete remission following the TGV treatment according to methods disclosed herein.

Example 5. TGV Therapy for Metastatic Prostate Cancer

The patient is a 71-year-old male referred for TGV therapy after being treated with all the standard hormonal therapies and chemotherapies for the treatment of metastatic prostate cancer, and one experimental therapy that failed. The patient was put on the TGV regimen and his PSA went from 600 to 16 with all bone pain completely disappearing. The treatment is being given every two weeks, the patient is continuing the TGV treatment according to methods disclosed herein.

Example 6. TGV Therapy for Leptomeningeal Breast Cancer

The patient was a 51-year-old woman with mucinous adenocarcinoma of the left breast. It had metastasized to her bones, brain, and leptomeninges. Leptomeningeal breast cancer has a survival rate of about 31 days. The patient was placed on TGV and, after just four months, she went into a complete remission, which lasted 3½ years before she succumbed to metastatic cancer in the liver.

Example 7. TGV Therapy for Glioblastoma Multiforme

The patient was a 61-year-old woman with glioblastoma multiforme. She approached for TGV therapy after having had a primary resection of most of her tumor some two years earlier. She was given radiation therapy and temozolomide, which put her into remission for two years. On relapse, she had another resection. Her tumor was tested for TGV therapy and it demonstrated sensitivity to TGV. She was put on the TGV regimen. She went into a complete remission, which lasted three years.

Example 8. TGV Therapy for Widely Metastatic Breast Cancer

The patient is a 41-year-old woman with neglected breast cancer and widely metastatic disease to bone, brain, spinal cord, lungs, and liver. She finally consented to having cytometric testing of her 14 cm fungating breast mass just prior to having regional chemotherapy into the left breast to control the smell and infection. Cytometric testing demonstrated TGV to be the most active agent and it was administered. The patient went into a remission of disease with approximately equal responses both inside and outside the blood brain barrier. The remission has lasted two and a half years.

Example 9. TGV Therapy for Lung Cancer

The patient is a 71-year-old male with plural effusion, right lower lobe adenocarcinoma of the lung with multiple brain metastasis. The patient was treated with TGV for four months, is in a near complete remission, and is continuing the TGV treatment according to methods disclosed herein with equal responses both inside and outside the blood brain barrier. Pleural effusion and approximately 90% of all the signs of cancer were treated and the patient has had very few side effects.

Example 10. TGV Therapy for Recurrent, Metastatic Bowel Cancer

The patient is a 75-year-old male with metastatic, recurrent large bowel cancer. He had been treated some 10 years earlier with 5-fluorouracil and oxaliplatin. He relapsed in the lower pelvis. The tumor was resected although there was clearly residual disease in the peritoneal cavity. The patient was treated with TGV and went into a two-year remission with six months of TGV treatment according to the disclosure.

Example 11. TGV Therapy for Triple-Negative Squamous Cell Carcinoma of the Breast A 44-year-old woman presented with squamous cell carcinoma of the breast, which was refractory to Cytoxan, Adriamycin, and Taxotere. Cytometric testing demonstrates that the most active agent was TGV. The patient was treated with six cycles of TGV. Her tumor had measured over 8 cm, but at the end of treatment there was no palpable disease. Her dramatic, complete remission was confirmed by an open biopsy. The patient was also given radiation therapy to the breast and remains in a complete clinical remission 2½ years after the TGV treatment according to methods disclosed herein.

Example 12. TGV Therapy for Triple-Negative, Lobular and Ductile Cancer of the Breast A 38-year-old woman presented with dumbbell-shaped, massive triple-negative mixed lobular and ductile carcinoma of the left breast. Cytometric testing was performed on both the ductal and the lobular components of this cancer and both were very sensitive to TGV. The patient was treated with TGV therapy and over eight cycles of TGV treatment according to methods disclosed herein (four months) all cancer disappeared, and the patient went on to receive radiation therapy to her breast, as her remission was pathologically complete on re-biopsy.

Example 13. TGV Therapy for Small Cell Lung Cancer

A 72-year-old woman with massive, enlarged liver from small cell cancer of the lung had cytometric testing performed. It was demonstrated that her small cell lung cancer was not sensitive to any standard drugs but was sensitive to TGV. The patient, who had about one month to live, was treated with the TGV treatment according to methods disclosed herein, and went into remission, and lived 18 months.

Example 14. TGV Therapy for Pancreatic Cancer

A 51-year-old patient presented with pancreatic cancer. Cytometric testing was performed on an incompletely resected cancer. The patient's most active treatment from this analysis was TGV, with no evidence of response to 5-fluorouracil, gemcitabine, oxaliplatin, or Taxotere, which are the standard agents for this disease. The patient received TGV for six months and is disease-free 3½ years after TGV treatment according to methods disclosed herein with no evidence of disease.

Example 15. TGV Therapy for Acute Myelogenous Leukemia 54-year-old male who failed standard induction chemotherapy for acute myelogenous leukemia with adverse molecular markers, and failed two other experimental therapies, presented with a white cell count of 234,000 cells per cubic millimeter (cmm) on hospice. Cytometric testing was performed, which demonstrated that he was sensitive to TGV and the TGV treatment was started. Within one week of treating the patient with the TGV treatment according to methods disclosed herein, his white count representing leukemia cells went from 234,000 down to 1000.

Example 16. TGV Therapy for Esthesioneuroblastoma

The patient is a 58-year-old former professional hockey player who developed a slow growing esthesioneuroblastoma. The disease did not respond to twelve years of treatments: surgery, radiation therapy, and multiple chemotherapies. The patient came for TGV therapy, and, after cytometric testing, TGV was indicated. The patient remains on TGV treatment according to methods disclosed herein and has a partial remission shown on MRIs. The patient continues to feel that he is substantially better and is tolerating the treatment with no significant toxicities.

Example 17. TGV Therapy for Urothelial Cancer

A 76-year-old male with regionally advanced bladder cancer was presented with urothelial cancer in the trigone of his bladder. The patient was treated with radiation therapy and with dose dense MVAC (M—methotrexate, V—vinblastine, A—doxorubicin, C—Cisplatin). The patient went into complete remission until six months later when retroperitoneal disease in the form of lymphadenopathy was discovered. The patient was then treated with gemcitabine and cisplatin to which he had no response. The patient then had the retroperitoneal lymph nodes radiated to a complete response. The patient was followed monthly and when recurrent disease was discovered in the lung and mediastinum, he was started on Padcev® (Enfortumab vedotin), to which he had no response. The patient was then offered TGV. Neulasta® (pegfilgrastim) was given with TGV, as the patient had been heavily pre-treated. The patient had neutropenia within five days and was admitted. A repeat PET-CT scan demonstrated no evidence of disease anywhere. It was concluded that the patient should not be given repeated chemotherapy until his bone marrow had recovered.

Example 18. TG as an Adjuvant to a Prescribed Treatment

A 38-year-old woman presented with a one-year history of metastatic carcinoma of the urachus. She was being treated with FOLFIRINOX (FOL—Leucovorin Calcium (Folinic Acid), F—Fluorouracil, IRIN—Irinotecan Hydrochloride, and OX—Oxaliplatin) without response. The patient was then referred for palliative care.

She had a large amount of ascites, which was removed and sent for cytometric testing. The testing revealed that the patient had sensitivity to 5-fluorouracil and hypersensitivity to gemcitabine and oxaliplatin. The patient was started on oral capecitabine with gemcitabine and oxaliplatin given every two weeks in a dose dense fashion.

Her initial carcinoembryonic antigen (CEA) antigen was 350. Over a period of 8 months this came down to a CEA of 21 and the patient felt that she was having difficulty tolerating further doses of chemotherapy despite the disappearance of all cancer symptoms. The patient was evaluated for surgery. The patient's surgical intervention resulted in resection of only necrotic debris none of which was viable microscopically or cytometrically.

The patient went off chemotherapy. Her CEA rose to 600 and symptoms increased. She was treated again with capecitabine, gemcitabine, and oxaliplatin. Her CEA went from 600 to 121 then spiked again, despite chemotherapy, up to 236. The patient had become resistant to capecitabine, gemcitabine, and oxaliplatin treatment. Having no other therapeutic options from cytometric analysis the patient was started on tamoxifen and gefitinib to inhibit the P glycoprotein and her CEA with the same therapy decreased to where it reached 62.

What is claimed:

1. A method of treating bladder cancer in a human subject comprising administering to the subject a regimen comprising administration of tamoxifen, gefitinib, and vinorelbine, wherein the regimen comprises administering tamoxifen and gefitinib concurrently twice daily, and vinorelbine once daily, for three days, and wherein:

tamoxifen is administered at a dose of about 60 mg/m$^2$ to about 80 mg/m$^2$ to the subject, twice daily;

gefitinib is administered at a dose of about 100 to about 187.5 mg/m$^2$ to the subject, twice daily; and vinorelbine is administered at a dose of about 5 to about 80 mg/m$^2$ to the subject, once daily.

2. The method of claim 1, wherein the regimen comprises administering tamoxifen and gefitinib concurrently twice daily for three consecutive days, and vinorelbine once daily on day 2 of the three consecutive days.

3. The method of claim 1, wherein the regimen is repeated every week, every two weeks, every three weeks, or every four weeks.

4. The method of claim 1, wherein gefitinib is administered at a dose of about 150 to about 187.5 mg/m$^2$ per administration.

5. The method of claim 1, wherein tamoxifen is administered at a dose of about 80 mg/m$^2$ per administration.

6. The method of claim 1, wherein vinorelbine is administered at a dose of about 10 to about 80 mg/m$^2$ per administration.

7. The method of claim 1, wherein the regimen comprises orally administering between about 150 and about 187.5 mg/m$^2$ of gefitinib to the subject, twice daily, on days 1, 2, and 3 of the regimen, orally administering between about 64 and about 80 mg/m$^2$ of tamoxifen to the subject, twice daily, on days 1, 2, and 3 of the regimen, and orally or intravenously administering an effective amount of vinorelbine to the subject on day 2 of the regimen.

8. The method of claim 1, wherein the vinorelbine is intravenously administered to the subject on day 2 of the regimen.

9. The method of claim 1, wherein the vinorelbine is orally administered to the subject on day 2 of the regimen.

10. The method of claim 1, wherein between about 10 and about 80 mg/m$^2$ of vinorelbine is administered to the subject on day 2 of the regimen.

11. The method of claim 1, wherein about 187.5 mg/m$^2$ of gefitinib is orally administered twice daily, on days 1, 2, and 3 of the regimen.

12. The method of claim 1, wherein about 80 mg/m$^2$ of tamoxifen is orally administered twice daily, on days 1, 2, and 3 of the regimen.

13. The method of claim 1, wherein about 80 mg/m$^2$ of vinorelbine is orally or intravenously administered on day 2 of the regimen.

14. The method of claim 1, wherein about 30 mg/m$^2$ of vinorelbine is orally or intravenously administered on day 2 of the regimen.

15. The method of claim 1, wherein the subject has a body surface area of 0.5 to 3.6 m$^2$.

16. The method of claim 1, wherein the regimen is repeated about every 2 weeks.

17. The method of claim 1, wherein the regimen is repeated about every 3 weeks.

18. The method of claim 1, wherein the cancer is stage I cancer, stage II cancer, stage III cancer, or stage IV cancer.

19. The method of claim 1, wherein the method results in a reduction in the size of the cancer tumor, as compared to the size of the cancer tumor prior to the method.

20. The method of claim 1, wherein the method results in a decrease in the level of a circulating cancer marker(s), as compared to the level of circulating cancer marker(s) prior to the method.

21. The method of claim 1, wherein the method results in an improvement in the subject's Anamnestic Comparative Self-Assessment (ACSA), as compared to the subject's ACSA prior to the method.

* * * * *